United States Patent [19]
Chatterjee et al.

[11] Patent Number: 5,965,399
[45] Date of Patent: Oct. 12, 1999

[54] CLONING AND EXPRESSION OF RAT LIVER AND PORCINE LIVER RIBONUCLEASE INHIBITOR

[75] Inventors: Deb K. Chatterjee, Potomac; Harini Shandilya, New Market, both of Md.

[73] Assignee: Life Technologies, Inc., Rockville, Md.

[21] Appl. No.: 08/795,395

[22] Filed: Feb. 4, 1997

Related U.S. Application Data

[63] Continuation-in-part of application No. 08/794,546, Feb. 3, 1997, abandoned
[60] Provisional application No. 60/024,057, Aug. 16, 1996, abandoned.
[51] Int. Cl.$^6$ .............................. C07H 21/04; C12P 21/06
[52] U.S. Cl. .................... 435/69.2; 435/69.1; 435/194; 435/252.33; 435/320.1; 536/23.1; 536/23.5; 536/23.4
[58] Field of Search .......................... 536/23.5; 435/194, 435/325, 252.3, 419, 252.33, 69.1, 69.2; 530/350

[56] References Cited

U.S. PATENT DOCUMENTS

| | | | |
|---|---|---|---|
| 4,966,964 | 10/1990 | Shapiro et al. | 536/27 |
| 5,019,556 | 5/1991 | Shapiro et al. | 514/2 |
| 5,266,687 | 11/1993 | Shapiro et al. | 536/23.1 |
| 5,552,302 | 9/1996 | Lewis et al. | 435/692 |

OTHER PUBLICATIONS

Vicentini et al., Biochemistry, vol. 29, No. 37, pp. 8827–8834, 1990.
Blackburn, P., et al., "Ribonuclease Inhibitor from Human Placenta," *J. Biol. Chem.* 252(16):5904–5910 (1977).
Blackburn, P., "Ribonuclease Inhibitor from Human Placenta: Rapid Purification and Assay," *J. Biol. Chem.* 254(24):12484–12487 (1979).
Burton, L.E., et al., "Ribonuclease Inhibitor From Bovine Brain," *Int. J. Pept. Prot. Res.* 16:359–364 (1980).
Burton, L.E., and Fucci, N.P., "Ribonuclease inhibitors from the livers of five mammalian species," *Int. J. Pept. Prot. Res.* 19:372–379 (1982).
Chopra, A.K., et al., "Improved synthesis of *Salmonella typhimurium* enterotoxin using gene fusion expression systems," *Gene* 144:81–85 (1994).

Gentz, R., et al., "Bioassay for trans–activation using purified human immunodeficiency virus tat–encoded protein: Trans–activation requires mRNA synthesis," *Proc. Natl. Acad. Sci. USA* 86:821–824 (1989).
Goldman, R.E., et al., "A procedure For The Rapid Preparation of $^{14}$C–Aminoacyl–Transfer RNA and Its Use in the Assay of Class I Ribonucleases and Ribonuclease Inhibitor," *Prep. Biochem.* 11(1):49–67 (1981).
Hofsteenge, J., et al., "Amino Acid Sequence of the Ribonuclease Inhibitor from Porcine Liver Reveals the Presence of Leucine–Rich Repeats," *Biochemistry* 27:8537–8544 (1988).
Humphreys, D.P., et al., "Human Protein Disulfide Isomerase Functionally Complements a dsbA Mutation and Enhances the Yield of Pectate Lyase C in *Escherichia coli*," *J. Biol. Chem.* 270(47):28210–28215 (Nov. 24, 1995).
Kawanomoto, M., et al., "cDNA cloning and sequence of rat ribonuclease inhibitor, and tissue distribution of the mRNA," *Biochem. Biophys. Acta* 1129:335–338 (1992).
Kobe, B., and Deisenhofer, J., "Crystal structure of porcine ribonuclease inhibitor, a protein with leucine–rich repeats," *Nature* 366:751–756 (1993).
Lee, F.S., et al., "Primary Structure of Human Placental Ribonuclease Inhibitor," *Biochemistry* 27:8545–8553 (1988).
Neumann, U., et al., "Crystallization of Porcine Liver Ribonuclease Inhibitor a Member of the Family of Proteins Containing Leucine–rich Repeats," *J. Mol. Biol.* 231:505–508 (1993).
Vicentini, A.M., et al., "Protein Chemical and Kinetic Characterization of Recombinant Porcine Ribonuclease Inhibitor Expressed in *Saccharomyces cerevisiae*," *Biochemistry* 29:8827–8834 (1990).
Wilson, I.A., et al., "The Structure of an Antigenic Determinant in a Protein," *Cell* 37:767–778 (1984).

*Primary Examiner*—Ponnathapura Achutamurthy
*Assistant Examiner*—Nashaat T. Nashed
*Attorney, Agent, or Firm*—Sterne, Kessler, Goldstein & Fox PLLC

[57] ABSTRACT

The invention relates to the cloning of a gene encoding rat liver ribonuclease inhibitor (RI), and its expression in a cellular host. In addition, the invention relates to the successful cloning of a gene encoding porcine liver RI, and its expression in a cellular host.

21 Claims, 3 Drawing Sheets

CLONING AND EXPRESSION OF RAT LIVER AND PORCINE LIVER RIBONUCLEASE INHIBITOR

The present application is a continuation-in-part of U.S. application Ser. No. 08/794,546, filed Feb. 3, 1997 (now abandoned), and claims the benefit of the filing date of U.S. Provisional Application No. 60/024,057, filed Aug. 16, 1996, abandoned.

BACKGROUND OF THE INVENTION

1. Field of the Invention

The invention relates to the successful cloning of a full length cDNA of porcine liver ribonuclease inhibitor (RI) gene and its expression in a cellular host. In addition, the invention relates to the cloning of full length rat liver RI, and its expression in a cellular host.

2. Related Art

RI is a cytoplasmic protein ubiquitously present in a variety of mammalian tissues. It inhibits a variety of ribonucleases (RNases) by binding tightly to both intracellular and extracellular RNases by forming a 1:I complex (Roth, J. S., *Methods Cancer Res.* 3:153–243 (1967); Blackburn, P. et al., *J. Biol. Chem.* 252:5904–5910 (1977); Blackburn, P., *J. Biol. Chem.* 254:12484–12487 (1979); Blackburn, P and Moore, S., *Enzymes*, 3rd Ed. (1982), vol. 15, pp. 317–433; Lee, F. S. et al., *Biochemistry* 27:8545–8553 (1988)). Some evidence indicates that tissues which are highly active in protein synthesis have a high excess of RI over RNase. Conversely, in catabolically active tissues that do not accumulate RNA, the ratio of RI to RNase is low (Kraft, N. and Shortman, K., *Biochim. Biophys. Acta.* 217:164–175 (1970)). The biological function of RI has been implicated to be in (a) regulation of RNA turnover by controlling cytoplasmic RNase activity, (b) safeguarding against non-cytoplasmic RNases that mislocalized to the cytoplasm, and (c) regulation of angiogenin, a protein that induces blood vessel growth and contains RNase activity. In vitro, RI is useful in a variety of molecular biology applications where RNase contamination is a potential problem. Examples of these applications include reverse transcription of mRNA, cell-free translation systems, preparation of RNase-free antibodies, and in vitro virus replication. Ideally, RI to be used in these kinds of applications will be capable of inhibiting a large number of RNases, such as eukaryotic RNase A, RNase B and RNase C, as well as prokaryotic RNases.

RI has been purified to homogeneity from several tissues, including placenta (Blackburn, P. et al., *J. Biol. Chem.* 252:5904–5910 (1977); Blackburn, P., *J. Biol. Chem.* 254:12484–12487 (1979)), brain (Burton, L. E. et al., *Int. J. Pept. Protein Res.* 16:359–364 (1980)), and liver (Burton, L. E. and Fucci, N. P., *Int. J. Pept. Protein Res.* 18:372–379 (1982); Hofsteenge, J. et al., *Biochemistry* 27:8537–8544 (1988)). The protein has an apparent molecular mass of approximately 50 kilodaltons (kD). The primary amino acid sequence of various RIs, such as human placental (Lee, F. S. et al., *Biochemistry* 27:8545–8553 (1988)), porcine liver (Hofsteenge, J. et al., *Biochemistry* 27:8537–8544 (1988)) and rat lung (Kawanomoto, M. et al., *Biochim. Biophys. Acta.* 1129:335–338 (1992)) is known. The crystal structure of porcine RI has been published (Kobe, B. and Deisenhofer, J., *Nature* 366:751–756 (1993)). The human placental RI has been successfully cloned and expressed in *E. coli* (Lee, F. S. et al., *Biochemistry* 27:8545–8553 (1988); Promega Catalog 1993/1994). A complete rat lung RI cDNA has been described by Kawanomoto et al. (*Biochim. Biophys. Acta.* 1129:335–338 (1992)); this cDNA has been used to study the distribution of the mRNA in various tissues.

The complete coding sequence of rat lung RI is known, but recombinant rat lung RI has not been expressed in either *E. coli* or any other known expression host (Kawanomoto, M., et al., *Biochim. Biophys. Acta* 1129:335–338 (1992)). Several attempts to isolate a cDNA clone for rat liver RI have been unsuccessful (Id).

The complete amino acid sequence of porcine RI has been determined by direct sequencing of the purified protein. In addition, a partial cDNA sequence of porcine kidney RI has been described by Vicentini, A. M. et al. (*Biochemistry* 29:8827–8834 (1990)). The cDNA lacks 241 nucleotides at the 5'-end of the coding sequence corresponding to the first 81 amino acids of porcine kidney RI. However, a synthetic complete porcine kidney RI coding sequence has been prepared by ligating a synthetic oligonucleotide encoding amino acid residues 1–81 of porcine RI, the sequence of which is based on the amino acid sequence of porcine liver RI, to a restriction fragment of the incomplete cDNA which corresponds to amino acid residues 82–456 of the above-mentioned cDNA. This protein has been expressed in *Saccharomyces cerevisiae*.

From the foregoing, it will be clear that there is a need in the art for recombinantly produced RNase inhibitors that are active against a broad range of RNases from both eukaryotic and prokaryotic sources.

SUMMARY OF THE INVENTION

The invention relates to the successful cloning of a full length cDNA of porcine liver RI gene and its expression in a cellular host.

More particularly, the invention relates to a composition comprising an isolated nucleic acid molecule comprising a nucleotide sequence encoding the complete coding sequence of porcine ribonuclease inhibitor (RI). In another embodiment, this nucleic acid molecule is operably linked to a promoter for expression of porcine RI. In another embodiment, the invention relates to a vector comprising this latter construct, which when introduced into a cellular host leads to expression of porcine RI. In another embodiment, the invention relates to a host cell comprising the above-described vector. The invention also relates to a method of obtaining porcine RI, comprising obtaining the host cell described above, and isolating porcine RI from it.

The invention also relates to the cloning of a cDNA encoding rat liver RI, and its expression in a cellular host.

More particularly, the invention relates to a composition comprising an isolated nucleic acid molecule comprising a nucleotide sequence encoding the complete coding sequence of rat ribonuclease inhibitor (RI), where the coding sequence is operably linked to a promoter for expression of rat RI. In another embodiment, the invention relates to a vector comprising the above described nucleic acid molecule which, when introduced into a cellular host, leads to expression of rat RI. In another embodiment, the invention relates to a host cell transformed with the above described vector. The invention also relates to a method for obtaining rat liver RNase inhibitor, comprising culturing this host cell and isolating rat RI from it.

DETAILED DESCRIPTION OF THE PREFERRED EMBODIMENTS

Definitions

Figure 1:
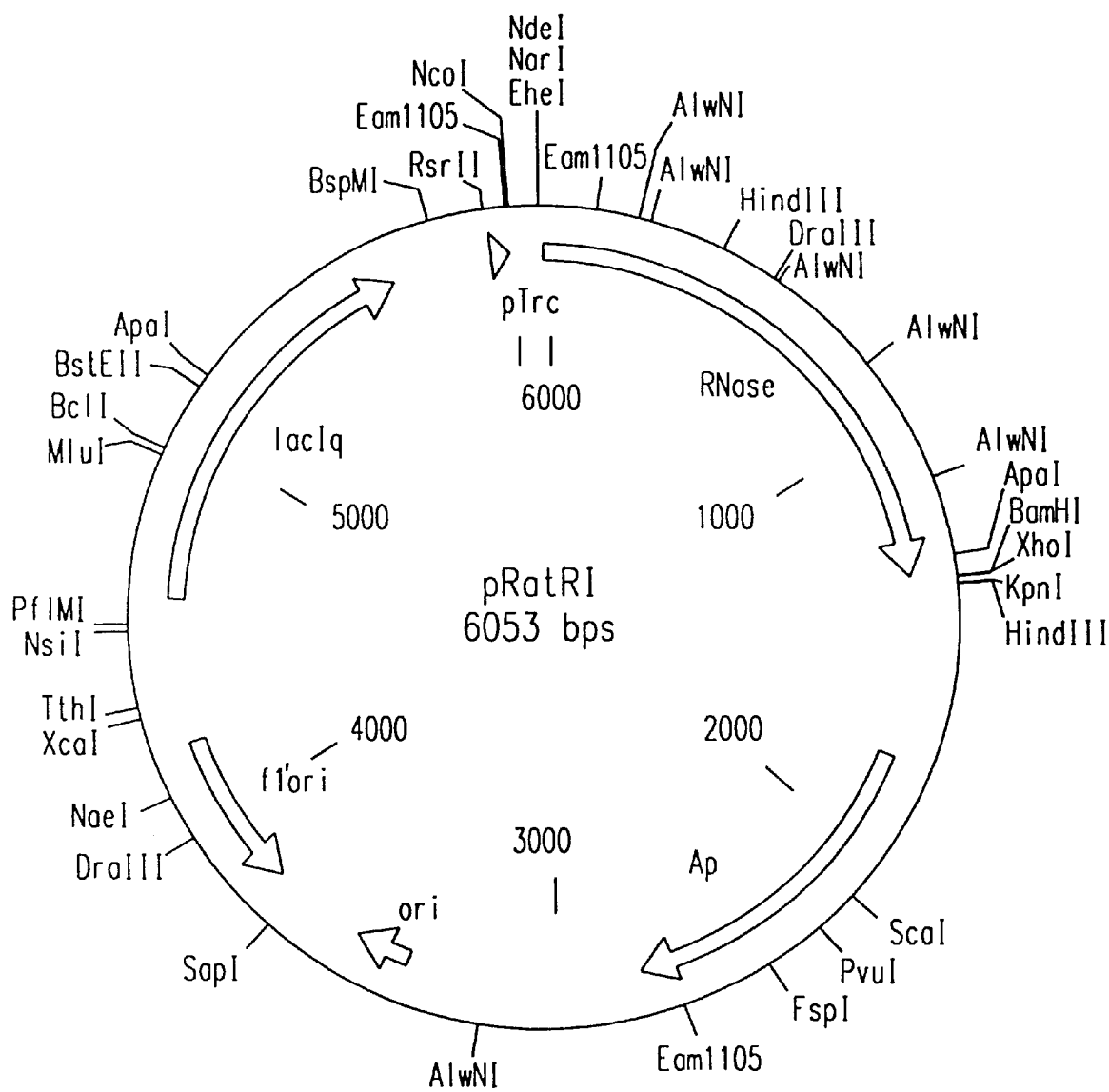
FIG. 1: A map of plasmid pRatRI.

In the description that follows, a number of terms used in recombinant DNA technology are utilized extensively. In order to provide a clear and consistent understanding of the specification and claims, including the scope to be given such terms, the following definitions are provided.

Cloning vector. A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector. A vector similar to a cloning vector but which is capable of expressing a gene which has been cloned into it, after transformation into a host. The cloned gene is usually placed under the control of (i.e., operably linked to) certain control sequences such as promoter sequences. Promoter sequences may be either constitutive, repressible or inducible.

Substantially pure. As used herein means that the desired purified protein is free from contaminating cellular components which would substantially inhibit the ribonuclease inhibiting activity of the protein. "Substantially pure" does not indicate that the protein must be completely free of all contaminants.

Substantially RNase Free. The terms "substantially RNase free" or "substantially free of RNase" are defined herein as having less than 10%, preferably about or loss than 1% and most preferably about or less than 0.1%, of the RNase activity found when purifying ribonuclease inhibitor with an RNase affinity column. For assays to determine RNase activity and ribonuclease inhibitor activity, see Goldman et al., *Prep. Biochem.* 11:49–67 (1981).

Recombinant Host. According to the invention, a recombinant host may be any prokaryotic or eukaryotic microorganism which contains the desired cloned genes on an expression vector or cloning vector. This term is also meant to include those microorganisms that have been genetically engineered to contain the desired gene(s) in the chromosome or genome of that organism.

Recombinant vector. Any cloning vector or expression vector which contains the desired cloned gene(s).

Host. Any prokaryotic or eukaryotic microorganism that is the recipient of a replicable expression vector or cloning vector. A "host," as the term is used herein, also includes prokaryotic or eukaryotic microorganisms that can be genetically engineered by well known techniques to contain desired gene(s) on its chromosome or genome. For examples of such hosts, see Maniatis et al., *Molecular Cloning: A Laboratory Manual*, Cold Spring Harbor Laboratory, Cold Spring Harbor, N.Y. (1982).

Promoter. A DNA sequence generally described as the 5' region of a gene, located proximal to the start codon. The transcription of an adjacent gene(s) is initiated at the promoter region. Promoters can be inducible, repressible or constitutive. Genes that are under the control of an inducible or repressible promoter are transcribed at levels that vary in response to the external environment. If a promoter is an inducible promoter, then the rate of transcription increases in response to an inducing agent. If a promoter is a repressible promoter, then the rate of transcription decreases in response to repressor (or negative regulator). It is possible for a promoter to be both inducible and repressible. Transcription from such a promoter will be inhibited in response to a repressor; this inhibition may be reversed by the action of an inducing agent. An example of such a promoter that is well known by those of ordinary skill in the art is the lac promoter. A description of the regulation of the lac promoter may be found in Lewin, *Genes V*, Oxford University Press, New York (1994). In contrast, if the promoter is a constitutive promoter, the rate of transcription is not regulated by the external environment.

Repression. Repression is the inhibition of transcription effected by the binding of repressor protein to a specific site on DNA.

Induction. Induction is the switching on of transcription as a result of interaction of an inducer with a positive or negative regulator.

Positive Regulation of Transcription. A mechanism of control of gene expression where a gene is not transcribed unless a positive regulator, or activator, allows initiation of transcription.

Negative Regulation of Transcription. A mechanism of control of gene expression where a gene is transcribed unless transcription is prevented by the action of a negative regulator, or repressor.

Repressor. A protein which prevents transcription by binding to a specific site on DNA.

Operator. The site on DNA at which a repressor protein binds to prevent transcription from initiating at the adjacent promoter.

Inducer. A molecule that triggers gene transcription by binding to a regulator protein such as a repressor.

Gene. A DNA sequence that contains information needed for expressing a polypeptide or protein.

Structural gene. A DNA sequence that is transcribed into messenger RNA (mRNA) that is then translated into a sequence of amino acids characteristic of a specific polypeptide.

Expression. Expression is the process by which a polypeptide is produced from a structural gene. The process involves transcription of the gene into mRNA and the translation of such mRNA into polypeptide(s).

Nucleic Acid Molecules and Polypeptides of the Invention

The invention relates to a composition comprising an isolated nucleic acid molecule comprising a nucleotide sequence encoding the complete coding sequence of porcine ribonuclease inhibitor (RI).

The invention also relates to a composition comprising an isolated nucleic acid molecule comprising a nucleotide sequence encoding the complete coding sequence of rat ribonuclease inhibitor (RI).

In a preferred embodiment, a sequence encoding either rat or porcine RI is operably linked to a promoter for expression of the RI protein. In another preferred embodiment, a sequence encoding either rat liver or porcine liver RI is operably linked to a promoter for expression of the RI protein.

In another preferred embodiment, the invention relates to a composition comprising an isolated nucleic acid molecule comprising a nucleotide sequence of porcine liver RI, wherein said nucleotide sequence is selected from the group consisting of:

(a) the sequence set forth in SEQ ID NO:1, wherein T can also be U;

(b) a nucleotide sequence encoding the porcine RI polypeptide having the complete amino acid sequence encoded by the cDNA clone contained in NRRL Deposit No. B-21612;

(c) a nucleotide sequence complementary to (a) or (b); and (d) fragments of (a) or (b) or (c) which fall within a portion of SEQ ID NO:1, wherein said fragments are at least 18 bases in length, and will hybridize to porcine genomic DNA encoding liver RI under stringent hybridization conditions. Preferably, the fragments fall within the portion of SEQ ID NO:1 that encodes the first 81 amino acids of porcine liver RI.

In another preferred embodiment, the invention relates to a composition comprising an isolated nucleic acid molecule comprising a nucleotide sequence of rat liver RI, wherein said nucleotide sequence is selected from the group consisting of:

(a) the sequence set forth in SEQ ID NO:3, wherein T can also be U;

(b) a nucleotide sequence encoding the rat RI polypeptide having the complete amino acid sequence encoded by the cDNA clone contained in NRRL Deposit No. B-21613;

(c) a nucleotide sequence complementary to (a) or (b); and (d) fragments of (a), (b) or (c) which fall within a portion of SEQ ID NO:3, wherein said fragments are at least 18 bases in length, and will hybridize to rat RI under stringent hybridization conditions.

By "stringent hybridization conditions" is intended overnight incubation at 42° C. in a solution comprising: 50% formamide, 5× SSC (150 mM NaCl, 15 mM trisodium citrate), 50 mM sodium phosphate (pH 7.6), 5× Denhardt's solution, 10% dextran sulfate, and 20 $\mu$g/ml denatured, sheared salmon sperm DNA, followed by washing the filters in 0.1× SSC at about 65° C.

Such nucleic acid molecules and fragments thereof are useful as DNA probes for detecting expression of RI in porcine or rat tissue by northern blot analysis, or as primers for amplification of a target sequence by the polymerase chain reaction (PCR).

Since the nucleotide sequences of porcine and rat liver RI are provided, generating such DNA fragments would be routine to the skilled artisan. For example, restriction endonuclease cleavage or shearing by sonication could easily be used to generate fragments of various sizes. Alternatively, the DNA fragments of the present invention could be generated synthetically according to known techniques.

The present invention also relates to vectors which include the isolated DNA molecules of the present invention, host cells which are genetically engineered with the recombinant vectors, and the production of rat liver or porcine liver RI polypeptides by recombinant techniques.

Eukaryotic and prokaryotic hosts that may be used for cloning and expressing the enzymes of the invention are well known in the art. Vectors which replicate in such host cells are also well known. The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; ptrc99a, pKK223-3, pKK233-3, pDR540, pRIT5 available from Pharmacia; and pUC18, pUC19 and pPROEX1, available from LTI. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Preferred prokaryotic hosts include, but are not limited to, bacteria of the genus Escherichia, Bacillus, Streptomyces, Pseudomonas, Salmonella, Serratia, Xanthomonas, etc. Two of the most preferred prokaryotic hosts are E. coli DH10B and DH5αF'IQ (available from LTI).

Host cells can be genetically engineered to incorporate nucleic acid molecules and express polypeptides of the present invention. For instance, recombinant constructs may be introduced into host cells using well known techniques of infection, transduction, transfection, and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques.

In accordance with this aspect of the invention the vector may be, for example, a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsulated virus by well known techniques for infection and transduction. Viral vectors may be replication competent or replication defective. In the latter case viral propagation generally will occur only in complementing host cells.

The present invention also encompasses the expression of rat liver or porcine liver RI in prokaryotic and eukaryotic cells. Therefore, preferred among vectors, in certain respects, are those for expression of the polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

In order to express the porcine or rat RI polypeptides of the invention, the polynucleotides encoding these genes generally will be inserted into the vector using standard techniques so that they are operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional coding sequence which codes for additional amino acids, such as those which provide additional fanctionalities. Thus, for instance, the polypeptide may be fused to a tag sequence, such as a peptide or leader peptide, which facilitates purification of the fused polypeptide. In certain preferred embodiments of this aspect of the invention, the marker sequence is a hexa-histidine peptide, such as the tag provided in the pPROEX1 vector (LTI), among others, many of which are commercially available. As described in Gentz et al., *Proc. Natl. Acad. Sci., USA* 86:821–824 (1989), for instance, hexa-histidine provides for convenient purification of the fusion protein. The polypeptide may also be fused to the (hemaglutinin) HA tag, which corresponds to an epitope derived of influenza hemaglutinin protein, described by Wilson et al., *Cell* 37:767 (1984), for instance. The fusion of the HA tag to the target protein allows easy detection of the recombinant protein with an antibody that recognizes the HA epitope. The sequence encoding the target protein may also be fused with sequence encoding the outer membrane protein A (OmpA) signal secretion sequence (21 amino acids) (Humphreys, D. P., et al., *J. Biol. Chem.* 270:28210–28215 (1995). Other tags that may be used for this purpose include the glutathione S-transferase (GST) tag and the thioredoxin tag (Chopra, A. K., et al., *Gene* (Amsterdam) 144: 81–85 (1994). Thus, for instance, a region of additional amino acids, particularly charged amino acids, may be added to the N-terminus of the polypeptide to improve stability and persistence in the host cell, during purification or during subsequent handling and storage. Also, regions may be added to the polypeptide to facilitate enhanced expression as well as purification. Such regions may be removed prior to final preparation of the polypeptide. The addition of peptide moieties to polypeptides to engender secretion or excretion, to improve stability and to facilitate purification, among others, are familiar and routine techniques in the art.

The DNA molecule inserted in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein. Polynucleotides of the invention, encoding the polypeptides of the invention, generally will be inserted into the vector using standard techniques so that they are operably linked to the promoter for expression. The polynucleotide will be positioned so that the transcription start site is located appropriately 5" to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

Hosts for of a great variety of expression constructs are well known, and those of skill will be enabled by the present disclosure readily to select a host for expressing a polypeptides in accordance with this aspect of the present invention.

Selection of appropriate vectors and promoters for expression in a host cell is a well known procedure and the requisite techniques for expression vector construction, introduction of the vector into the host and expression in the host are routine skills in the art.

Following transformation of a suitable host strain and growth of the host strain to an appropriate cell density, where the selected promoter is inducible, expression of the RI of the invention is induced by appropriate means (e.g., temperature shift or exposure to chemical inducer) and cells are cultured for an additional period.

In a preferred embodiment, the plasmid pPROEX1 is used for the expression of either rat or porcine RI. pPROEX1 contains the gene for the lacI$^q$ repressor, which blocks expression of the inserted gene of interest (here, the gene encoding porcine or rat RI) by binding to the lac operator unless an inducer such as isopropylthiogalactoside (IPTG) is present.

Of course, it will be understood by those of skill in the art that other inducers besides IPTG can be utilized where the RI gene is under the control of a lacI$^q$-repressible promoter, including but not limited to other thiogalactosides.

Where porcine RI is to be expressed, it is particularly preferred that the host cell expressing the porcine RI be a cell that constitutively expresses the repressor which controls porcine RI expression (see Example 2). Therefore, a particularly preferred method of expressing porcine RI comprises transforming a vector, which comprises the gene encoding porcine RI under the control of the lac promoter, into a host cell which constitutively expresses the lac repressor, and then inducing expression of porcine RI after the cells have grown to a sufficient density, such as an A590 of between about 0.6 and 1.0.

It will thus be understood by those of ordinary skill that other expression systems may be utilized, so long as the expression of porcine liver RI is tightly controlled. In such an expression system, the host cell harboring the porcine RI gene can be grown to a desired cell density, at which point expression of porcine RI can be initiated.

In order to obtain the RI, cells typically are then harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents; such methods are well know to those skilled in the art.

The rat liver RI or porcine liver RI polypeptide can be recovered and purified from recombinant cell cultures by well-known methods including ammonium sulfate precipitation, anion or cation exchange chromatography, phosphocellulose chromatography, hydrophobic interaction chromatography, affinity chromatography, hydroxyapatite chromatography and lectin chromatography. Most preferably, affinity chromatography is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The invention also relates to a general method of producing ribonuclease inhibitor which is substantially free of RNase activity. Such methods apply to purification of any ribonuclease inhibitor, regardless of the source. Thus, the general method of the invention relates to isolating substantially RNase free ribonuclease inhibitor from a biological sample (e.g., cells, tissue, skin, brain, liver, kidney, etc.) obtained from any mammalian source (e.g., human, rat, porcine, monkey, ape, bovine, etc.). In particular, the method of the invention for obtaining substantially RNase free ribonuclease inhibitor comprises (a) obtaining a biological sample from a mammalian source which contains a ribonuclease inhibitor, (b) mixing said sample with a binding partner, with the proviso that said binding partner is not an RNase, and (c) isolating ribonuclease inhibitor bound to said binding partner. In accordance with the invention, the binding partner may be any molecule, other than RNase, which reversibly binds ribonuclease inhibitor. Preferably, such binding partner is an antibody or an antibody fragment (e.g., Fab) having specificity for ribonuclease inhibitor, although other suitable binding partners will be readily apparent to one of skill in the art. In the preferred method of the invention, ribonuclease inhibitor is isolated or purified by affinity chromatography, wherein said binding partner is attached to a solid support (e.g., any column matrix including but not limited to sepharose, agarose, hydroyapatite, etc.).

The invention also provides a general method for obtaining recombinant ribonuclease inhibitor which is substantially free of RNase activity. Such a method is suitable for isolating and purifying any recombinant ribonuclease inhibitor, regardless of the type of the ribonuclease inhibitor (human, bovine, porcine, rat, monkey, ape, etc.) and regardless of the recombinant host used to express the ribonuclease inhibitor. In this method of the invention, substantially RNase free recombinant ribonuclease inhibitor is obtained by (a) culturing a recombinant host under conditions sufficient to express ribonuclease inhibitor, (b) mixing said ribonuclease inhibitor with a binding partner, with the proviso that said binding partner is not an RNase, and (c) isolating said ribonuclease inhibitor bound to said binding partner. In accordance with this aspect of the invention, the binding partner may be any molecule which binds to the ribonuclease inhibitor (e.g., antibodies and fragments thereof) provided however that said binding partner is not RNase.

Preferably, the recombinant ribonuclease is expressed in a modified form which allows selective binding to the binding partner. Such modifications which allow the isolation of a desired protein with a binding partner will be apparent to one skilled in the art. Preferably, the RI is modified to comprise a peptide to form a fusion protein which specifically binds to the binding partner (referred to herein as a "binding peptide"). Such peptide tags are well known in the art. Preferred peptide tags include His tag, thioredoxin tag, hemaglutinin tag, GST tag, and OmpA signal sequence tag. As will be understood, the binding partner which recognizes and binds to the binding peptide may be any molecule or compound including metal ions (e.g., metal affinity columns), antibodies or fragments thereof and any protein or peptide which binds the binding peptide. Thus, the invention relates to a method of obtaining substantially RNase free recombinant ribonuclease inhibitor comprising (a) culturing a recombinant host under conditions sufficient to express a ribonuclease inhibitor which comprises a binding peptide, (b) mixing said ribonuclease inhibitor with a binding partner which is capable of binding to said binding peptide, and (c) isolating said ribonuclease inhibitor bound to said binding partner. Preferably, the binding partner which binds the binding peptide is bound to a solid support (e.g., affinity chromatography).

The method of the invention may also comprise removing the binding peptide from RI after isolating or purifying the recombinant RI. Such removal may be accomplished by well known chemical and enzymatic techniques.

Having now generally described the invention, the same will be more readily understood through reference to the following Examples which are provided by way of illustration, and are not intended to be limiting of the present invention, unless specified.

EXAMPLES

Example 1
Cloning and Expression of Rat Liver RI in *E. coli*

To clone the gene encoding rat liver RI, total mRNA was isolated from rat liver, and first strand cDNA synthesis was accomplished using the protocol as previously described (Nathan, M. et al., *Focus* 17:78–80 (1995)). The oligonucleotide used at the 5'-end of the gene was (SEQ ID NO:5) 5' TAA TAG CAT ATG AGT CTT GAC ATC CAG TGT GAG 3'. The oligonucleotide used at the 3'-end of the gene was (SEQ ID NO:6) 5' TTA TTA GGA TCC TTA TCA GGA AAT GAT CCT CAG GGA TGG CC 3'. An NdeI and a BamHI site were created in the oligonucleotide (bold and underlined) for easy cloning into an expression vector. The oligonucleotides were designed based on the cDNA sequence of rat lung RI cDNA, and were obtained from LTI.

PCR was done using the PCR Supermix (LTI), which contains Taq DNA polymerase, plus about 10–20 ng of cDNA and oligonucleotides at a concentration of 2.5 $\mu$M. A Perkin-Elmer 9600 PCR machine was used to carry out the following cycling procedure: 1 cycle 94° C. for 5 min.; 30 cycles of 94° C. for 20 sec., 55° C. for 20 sec., 72° C. for 1 min.; 1 cycle 72° C. for 5 min.

The PCR fragment was digested with NdeI and BamHI and cloned into the pPROEX1 expression vector digested with NdeI and BamHI, which was obtained from LTI (Gaithersburg, Md.). This plasmid was then transformed into *E. coli* DH10B, a strain which was obtained from LTI. Six clones were picked to test whether they contained the cloned PCR product. Five out of 6 clones contained the cloned fragment. One of the clones, pRatRI (FIG. 1), was grown to express the rat liver RI, the amino acid sequence of which is given in SEQ ID NO:4. Proteins isolated from induced cultures (40 ml) grown at 30° C. and 37° C. were analyzed by SDS-polyacrylamide gel electrophoresis (SDS-PAGE) (Laemmli, U. K., *Nature* 227:680–685 (1970).

The pPROEX1 vector encodes 23 amino acid residues prior to the NdeI site. This region contains six histidine residues, a spacer region and a TEV-protease site. Thus, cloning at the NdeI site created a fusion protein containing an additional 23 amino acids at the amino terminus. Both the induced culture grown at 30° C. and the induced culture grown at 37° C. produced a protein slightly larger than 50 kD (about 52 kD), although RI purified from rat liver has a molecular weight of about 50 kD. The increase in the size of rat RI expressed from *E. coli* was due to the additional 24 amino acids corresponding to vector sequence. Although total RI protein production was higher at 37° C. than at 30° C., more soluble protein was produced at 30° C. Therefore, the cells appeared to produce more inclusion bodies at 37° C. than at 30° C.

Since the construction in pPROEX1 produced a fusion protein, an attempt to produce an unfused authentic rat liver RI was made. The NdeI-BamHI fragment from pRatRI was subcloned into pRE1 at the NdeI-BamHI sites. Plasmid pRE1, obtained from Dr. McKenney (Reddy, P. et al., *Nucleic Acids Res.* 17: 10473–10488 (1989)), is an expression vector containing a lambda pL promoter. The ligated material was introduced into CJ374 containing the repressor C1857 in a compatible chloramphenicol resistance plasmid (pCJ136). Six clones were tested for the presence of the cloned fragment, and six out of six clones contained the insert. One of the clones, pRERatRI (FIG. 2), was used to study the level of expression of RI.

Figure 2:
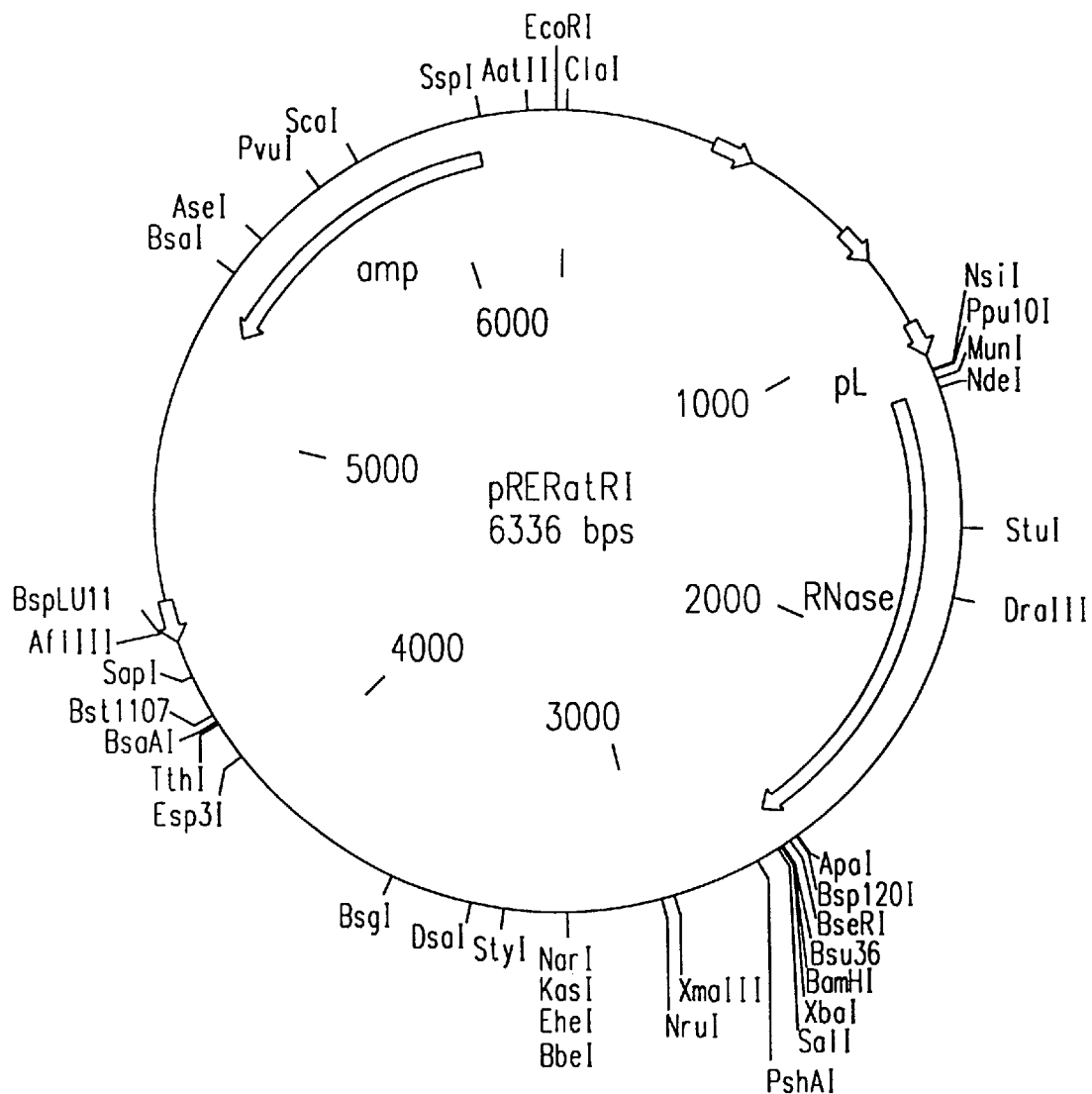
FIG. 2: A map of plasmid pRERatRI.

A 50 ml culture was grown in rich medium (20 g NZ amine, 10 g Yeast Extract, 5g NaCl, 2.5 g $K_2$ $HPO_4$, 0.4 g $MgSO_4$, 5 ml glycerol, pH 7.2), containing both ampicillin and chloramphenicol at 30° C. to an A590 of about 0.8. The culture was induced at 42° C. for 30 min and outgrown at 30° C. Samples were withdrawn for analysis by SDS-PAGE at different times. No induced protein around 50 kD was detected at any induction time point up to 4 hrs. Surprisingly, rat RI was only produced as a fusion protein. In order to find out whether fusion is necessary for expression of rat liver RI, the RI coding sequence was fused with an OmpA signal sequence (21 amino acids) and cloned in pRE1 (FIG. 2). The cells were grown as described above, and the samples were analyzed by SDS-PAGE. An expressed protein of about 50 kD was detected in the induced sample but not in the uninduced samples. Since the expected size of fused protein was 52 kD, and the induced soluble protein was about 50 kD, it was apparent that the protein was made as a fused protein and later processed to authentic RI without the signal sequence. This confirms that rat RI protein expresses well when produced as a fusion protein in *E. coli*. However, the fusion partner is dispensable following expression, as was shown with the OmpA-RI fusion.

Example 2
Cloning and Expression of Porcine Liver RI

In order to obtain the gene encoding porcine liver RI, total mRNA was isolated from porcine liver, and first strand cDNA synthesis was accomplished using the protocol as previously described (Nathan, M. et al., *Focus* 17:78–80 (1995)). Because the complete sequence of the porcine liver RI gene had not been established (Vincentini et al., *Biochemistry* 29: 8827–8834 (1990), the oligonucleotide used at the 5'-end of the gene corresponded to the amino-terminal amino acid sequence of porcine liver RI protein, while the oligonucleotide used at the 3'-end of the gene corresponded to the carboxy-terminal sequence of the porcine kidney RI gene. The nucleotide sequences of the oligonucleotide used at the 5'-end of the gene, which included a NdeI site (bold and underlined) was (SEQ ID NO:7) 5' TAT TAT CAT ATG AAC CTG/C GAC/T ATC/T CAC/T TGC/T GA 3'. The oligonucleotide used at the 3'-end of the gene (bold and underlined) was (SEQ ID NO:8) 5'TAT TAT AAG CTT GCC CAA AAG GTG TTT TAC TAA GTA G 3'.

PCR was carried out as described above in Example 1. The PCR products and the expression vector pPROEX1 were digested with NdeI and HindIII. The PCR products were then ligated into the vector, and the ligated material was introduced into DH10B, obtained from LTI (Gaithersburg, Md.). Surprisingly, very few clones were found. The PCR was repeated, and the fragment cloned again into pPROEX1. Only two out of 30 clones tested were found to have the insert. However, upon digestion with NdeI and HindIII, both clones generated a fragment of only about 1250 bp, rather than the 1500 bp of the PCR fragment. To confirm that the result was not a gel artifact, restriction digestion analysis was performed. The results suggest that the insert was indeed smaller than the PCR product. Interestingly, the two clones generated an identical restriction digestion profile.

The cloned fragment was also sequenced from both ends (see Example 3). The sequencing results indicate that both the amino and the carboxy termini of porcine liver RI were intact. These experiments indicate that the region deleted from the PCR fragment was internal to the porcine RI gene. The clone produced a protein of about 48 kD in size, smaller than the expected size of slightly greater than 50 kD. This smaller protein displayed no RI activity. From all of these experiments it was apparent that porcine RI is inhibitory to the growth of *E. coli*, and that the cloning procedure that was successful for obtaining the gene for rat liver RI was unsuitable for obtaining porcine liver RI. This result was surprising; as rat and porcine RI have 75% sequence identity, the clones were expected to have similar properties when expressed in *E. coli*. The reasons that porcine RI was difficult to clone and express in *E. coli* are unclear, but one theory is that porcine RI is so toxic to *E. coli* that the cell cannot express sufficient repressor in time to completely inhibit RI expression.

Figure 3:
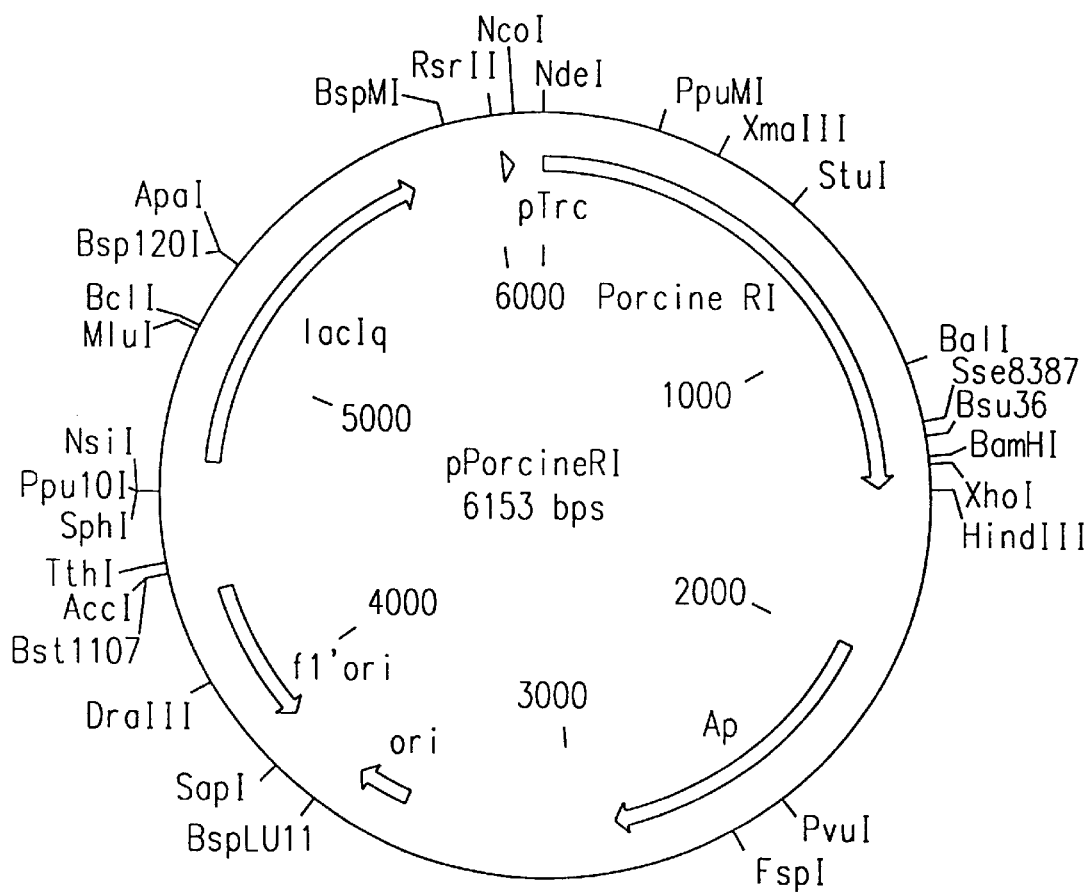
FIG. 3: A map of plasmid pPorcineRI.

The 1500 bp PCR product of the porcine RI gene was then cloned into the vector pUC18 digested by NdeI and HindIII, which lacks a promoter to drive the gene. These clones were stable. The NdeI-HindIII fragment containing the porcine RI gene was then subcloned into pPROEX1 digested with NdeI and HindIII, and the resulting plasmid was introduced into DH5αF'IQ, a strain which constitutively expresses lacI$^q$ so that the repressor is present even before the introduction of the expression plasmid containing an additional copy of lacI$^q$. Twelve transformants were tested for the insert. 12 out of 12 clones generated a correct sized fragment. One of the clones, pPorcineRI (FIG. 3), was tested further for expression of porcine RI, the amino acid sequence of which is given in SEQ ID NO:2. The recombinant host cell comprising pPorcineRI, *E. coli*(pPigRI), was deposited on Aug. 9, 1996, with the Collection, Agricultural Research Culture Collection (NRRL), 1815 North University Street, Peoria, Ill. 61604 USA, as Deposit No. NRRL B-21612.

*E. coli* DH5αF'IQ containing pPorcineRI was grown to an A590 of between about 0.6–1.0 in a rich medium (20 g NZ amine, 10 g Yeast Extract, 5 g NaCl, 2.5 g K$_2$HPO$_4$, 0.4 g MgSO$_4$, 5 ml glycerol, pH 7.2) and 100 μg/ml ampicillin at 30° C. The culture was induced with IPTG (1.5 mM) for 3 hrs. The culture was spun down and the pellets were stored at −70° C. until used. The clone produced a protein slightly larger than 50 kD as expected. Thus, by the unusual procedure of preprotecting the expression of porcine RI, porcine liver RI was successfully cloned and expressed in *E. coli*. Upon induction, however, the growth rate of *E. coli* expressing porcine RI diminished considerably, whereas no inhibition of growth was observed in *E. coli* expressing rat liver RI.

The problems encountered in cloning and expressing porcine RI in *E. coli* allow a prediction that porcine RI will be active against *E. coli* RNases in addition to RNaseA, B and C.

Example 3

DNA Sequence Analysis of Porcine Liver RI

The nucleotide sequence of the 243 nucleotides (encoding 81 amino acids) at the 5'-end of the RI gene was obtained by methods known in the art (SEQ ID NO:1, nucleotides 1–243). The amino acid sequence deduced from the nucleotide sequence of the cDNA matched perfectly with the amino acid sequence derived from direct sequencing of purified porcine RI.

Example 4

Purification of RI

All steps were carried out at 4° C. or on ice unless specified. The cells containing the recombinant plasmid were suspended at a 1:3 ratio (g. of cells:ml buffer) in a buffer consisting of 50 mM Tris-HCl pH 8.0, 100 mM KCl, and 10 mM beta-mercaptoethanol (β-ME). The cell suspension was subjected to sonication using a sonicator (Heat Systems) until 80% of the cells were cracked as measured by A590. The cell debris was clarified by centrifugation. The supernatant was filtered through a 5 μm acrodisc filter before loading onto a Ni-NTA-agarose affinity column equilibrated with 20 mM Tris-HCl, pH 8.0, 100 mM KCl, 10 mM β-ME, 10% glycerol. The column was washed with 10 column volume of equilibration buffer containing 20 mM imidazole. The RI was eluted using a linear gradient of imidazole ranging from 20 mM to 150 mM in the same buffer. The fractions were analyzed by SDS-PAGE for the presence of a 52 kD protein, the apparent size of the fused RI.

Fractions containing the expected 52 kD protein were pooled and dialyzed in a buffer containing 20 mM Tris-HCl, pH 7.5, 10 mM dithiothreitol (DTT), 10% glycerol. The dialyzed material was loaded onto a MonoQ column (Pharmacia) equilibrated with the same buffer. The column was washed with 10 column volumes of the same buffer. The RI was eluted using a linear gradient of KCl ranging from 0 mM to 500 mM in the same buffer.

The fractions were analyzed by SDS-PAGE, and fractions containing a 52 kD protein were pooled. The pooled material was dialyzed in a storage buffer containing 20 mM Tris-HCl, pH 7.5, 50 mM KCl, 10 mM DTT, and 50% glycerol. The sample was tested for RNase inhibitor activity.

Example 5

Assay for RNase Inhibitor Activity

The activity of RI was determined essentially as described by Blackburn, P. et al. (*J. Biol. Chem.* 252:5904–5910 (1977)). RNase inhibitor activity was expressed by its ability to inhibit the activity of 5 ng of RNaseA (as measured by hydrolysis of yeast RNA) by 50%.

Example 6

Stabilization of RNase Inhibitor Activity

The addition of a chelator (e.g., EDTA) was found to stabilize storage of RNase inhibitor purified over a Ni-NTA agarose affinity column (see Example 4). Samples stored without chelator were found stable at 4° C. for less than one month, while RI stored in the presence of a chelator were stable for greater than 6 months at 4° C.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following Claims. All patents and publications cited herein are incorporated by reference herein in their entirety.

What is claimed is:

1. An isolated nucleic acid molecule comprising a nucleotide sequence encoding a ribonuclease inhibitor (RI), wherein said nucleotide sequence is selected from the group consisting of:
    (a) the sequence set forth in SEQ ID NO:1, wherein T can also be U;
    (b) the nucleotide sequence contained in NRRL Deposit No. B-21612; and
    (c) a nucleic acid sequence complementary to (a) or (b).

2. The nucleic acid molecule of claim 1, wherein said RI sequence is set forth in SEQ ID NO:1.

3. The nucleic acid molecule of claim 1, further comprising a nucleotide sequence encoding a binding peptide.

4. The nucleic acid molecule of claim 3, wherein said sequence encoding a binding peptide is located 5' to the translation start site of said RI sequence.

5. The nucleic acid molecule of claim 3, wherein said binding peptide is selected from the group consisting of the OmpA signal sequence, a GST tag, a HIS tag, a thioredoxin tag, and a hemaglutinin (HA) tag.

6. The nucleic acid molecule of claim 1, wherein said sequence is operably linked to a promoter for expression of said RI.

7. A vector comprising the nucleic acid molecule of claim 1, wherein said sequence is operably linked to a promoter so that RI may be expressed when introduced into a cellular host.

8. The vector of claim 7, wherein said promoter is an inducible promoter.

9. The vector of claim 8, wherein said inducible promoter is under the control of a repressor.

10. The vector of claim 9, wherein said repressor is lacI$^q$.

11. A host cell comprising the vector of claim 7.

12. The host cell of claim 11, wherein said host cell is *Escherichia coli*.

13. A method of obtaining an isolated RI, comprising culturing the host cell of claim 11 and isolating said RI.

14. A method of obtaining substantially RNase free recombinant ribonuclease inhibitor, said method comprising
    (a) culturing a recombinant host comprising a nucleotide sequence encoding a ribonuclease inhibitor under conditions sufficient to express said recombinant ribonuclease inhibitor;
    (b) mixing said ribonuclease inhibitor with a binding partner molecule, with the proviso that said binding partner molecule is not an RNase; and (c) isolating said ribonuclease inhibitor from said binding partner molecule, wherein said nucleotide sequence encoding said ribonuclease inhibitor is selected from the group consisting of (i) the nucleotide sequence set forth in SEQ ID NO:1, wherein T can also be U; (ii) the nucleotide sequence contained in NRRL Deposit No. B-21612; and (iii) a nucleic acid sequence complementary to (a) or (b).

15. The method of claim 14, wherein said ribonuclease inhibitor comprises a binding peptide which specifically binds to said binding partner molecule.

16. The method of claim 15, wherein said binding peptide is selected from a group consisting of a HIS tag, a thioredoxin tag, a hemaglutinin tag, a GST Tag, and an OmpA signal sequence tag.

17. The method of claim 14, wherein said binding partner molecule is attached to a solid support.

18. The method of claim 14, wherein said binding partner molecule is an antibody or a fragment thereof.

19. The method of claim 14, wherein said host cell is a prokaryotic cell.

20. The method of claim 19, wherein said host cell is an Escherichia cell.

21. The method of claim 20, wherein said host cell is an *Escherichia coli* cell.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 1371 base pairs
       (B) TYPE: nucleic acid
       (C) STRANDEDNESS: both
       (D) TOPOLOGY: both (ii) MOLECULE TYPE: cDNA (ix) FEATURE:
       (A) NAME/KEY: CDS
       (B) LOCATION: 1..1368

(xi) SEQUENCE DESCRIPTION: SEQ ID NO:1:

```
ATG AAC CTC GAT ATT CAT TGC GAG CAG CTG AGC GAC GCC CGG TGG ACA        48
Met Asn Leu Asp Ile His Cys Glu Gln Leu Ser Asp Ala Arg Trp Thr
 1               5                  10                  15

GAG CTC CTG CCG CTG CTC CAG CAG TAT GAG GTG GTC AGG CTC GAC GAC        96
Glu Leu Leu Pro Leu Leu Gln Gln Tyr Glu Val Val Arg Leu Asp Asp
             20                  25                  30

TGC GGC CTC ACG GAG GAG CAC TGC AAG GAC ATC GGT TCT GCC CTC CGG       144
Cys Gly Leu Thr Glu Glu His Cys Lys Asp Ile Gly Ser Ala Leu Arg
         35                  40                  45

GCC AAC CCC TCC CTG ACC GAG CTC TGC CTC CGC ACC AAC GAG CTG GGC       192
Ala Asn Pro Ser Leu Thr Glu Leu Cys Leu Arg Thr Asn Glu Leu Gly
     50                  55                  60

GAT GCC GGC GTG CAC CTG GTG CTG CAG GGC CTG CAG AGC CCC ACC TGC       240
Asp Ala Gly Val His Leu Val Leu Gln Gly Leu Gln Ser Pro Thr Cys
 65                  70                  75                  80

AAG ATC CAG AAG CTC AGC CTG CAG AAC TGC TCC CTG ACC GAG GCG GGC       288
Lys Ile Gln Lys Leu Ser Leu Gln Asn Cys Ser Leu Thr Glu Ala Gly
                 85                  90                  95

TGC GGG GTC CTG CCC AGC ACG CTG CGC TCC CTG CCC ACG CTG CGG GAG       336
Cys Gly Val Leu Pro Ser Thr Leu Arg Ser Leu Pro Thr Leu Arg Glu
            100                 105                 110

CTG CAT CTC AGC GAC AAC CCA CTG GGG GAC GCC GGC CTG CGG CTG CTC       384
Leu His Leu Ser Asp Asn Pro Leu Gly Asp Ala Gly Leu Arg Leu Leu
        115                 120                 125

TGT GAG GGG CTC CTG GAC CCC CAG TGC CAC CTG GAG AAG CTG CAG TTG       432
Cys Glu Gly Leu Leu Asp Pro Gln Cys His Leu Glu Lys Leu Gln Leu
    130                 135                 140

GAG TAC TGC CGC CTG ACG GCC GCC AGC TGC GAG CCC CTG GCC TCG GTG       480
Glu Tyr Cys Arg Leu Thr Ala Ala Ser Cys Glu Pro Leu Ala Ser Val
145                 150                 155                 160

CTC AGG GCC ACG CGG GCC TTG AAG GAG CTC ACG GTG AGC AAC AAC GAC       528
Leu Arg Ala Thr Arg Ala Leu Lys Glu Leu Thr Val Ser Asn Asn Asp
                165                 170                 175

ATC GGC GAG GCC GGC GCC CGG GTG CTG GGC CAG GGT CTG GCA GAC TCT       576
Ile Gly Glu Ala Gly Ala Arg Val Leu Gly Gln Gly Leu Ala Asp Ser
            180                 185                 190

GCC TGC CAG CTG GAG ACG CTC AGG CTG GAG AAC TGC GGT CTC ACG CCA       624
Ala Cys Gln Leu Glu Thr Leu Arg Leu Glu Asn Cys Gly Leu Thr Pro
        195                 200                 205

GCC AAC TGC AAA GAC CTG TGC GGA ATT GTG GCC TCC CAG GCC TCG CTG       672
Ala Asn Cys Lys Asp Leu Cys Gly Ile Val Ala Ser Gln Ala Ser Leu
    210                 215                 220
```

```
AGG GAG CTT GAC CTG GGC AGC AAC GGG CTG GGC GAC GCG GGC ATA GCC    720
Arg Glu Leu Asp Leu Gly Ser Asn Gly Leu Gly Asp Ala Gly Ile Ala
225                 230                 235                 240

GAG CTG TGC CCC GGG CTC TTG AGC CCC GCC TCC CGC CTC AAG ACC CTG    768
Glu Leu Cys Pro Gly Leu Leu Ser Pro Ala Ser Arg Leu Lys Thr Leu
            245                 250                 255

TGG CTC TGG GAG TGT GAC ATC ACC GCC AGT GGC TGC AGA GAC CTC TGC    816
Trp Leu Trp Glu Cys Asp Ile Thr Ala Ser Gly Cys Arg Asp Leu Cys
                260                 265                 270

CGT GTC CTC CAG GCC AAG GAG ACC CTG AAG GAG CTC AGT CTG GCG GGC    864
Arg Val Leu Gln Ala Lys Glu Thr Leu Lys Glu Leu Ser Leu Ala Gly
            275                 280                 285

AAC AAG CTG GGC GAC GAG GGC GCC CGG CTG CTG TGC GAG AGC CTG CTG    912
Asn Lys Leu Gly Asp Glu Gly Ala Arg Leu Leu Cys Glu Ser Leu Leu
290                 295                 300

CAG CCC GGC TGC CAG CTG GAG TCC CTG TGG GTG AAG TCC TGC AGC CTC    960
Gln Pro Gly Cys Gln Leu Glu Ser Leu Trp Val Lys Ser Cys Ser Leu
305                 310                 315                 320

ACG GCG GCC TGC TGC CAG CAC GTC AGC TTG ATG CTG ACC CAG AAC AAG   1008
Thr Ala Ala Cys Cys Gln His Val Ser Leu Met Leu Thr Gln Asn Lys
            325                 330                 335

CAT CTC CTG GAA CTT CAG TTG AGC AGC AAC AAG CTG GGT GAC TCT GGC   1056
His Leu Leu Glu Leu Gln Leu Ser Ser Asn Lys Leu Gly Asp Ser Gly
                340                 345                 350

ATC CAG GAG CTG TGC CAG GCC CTG AGC CAG CCG GGC ACC ACA CTG CGG   1104
Ile Gln Glu Leu Cys Gln Ala Leu Ser Gln Pro Gly Thr Thr Leu Arg
            355                 360                 365

GTG CTC TGT CTT GGG GAC TGT GAG GTG ACC AAC AGC GGC TGC AGC AGC   1152
Val Leu Cys Leu Gly Asp Cys Glu Val Thr Asn Ser Gly Cys Ser Ser
370                 375                 380

CTC GCC TCG CTC CTG CTG GCC AAC CGC AGC CTG CGA GAG CTG GAC CTG   1200
Leu Ala Ser Leu Leu Leu Ala Asn Arg Ser Leu Arg Glu Leu Asp Leu
385                 390                 395                 400

AGC AAC AAC TGT GTG GGC GAC CCG GGC GTC CTG CAG CTG CTG GGG AGC   1248
Ser Asn Asn Cys Val Gly Asp Pro Gly Val Leu Gln Leu Leu Gly Ser
            405                 410                 415

CTG GAG CAG CCG GGC TGC GCC CTG GAG CAG CTG GTC CTG TAC GAC ACC   1296
Leu Glu Gln Pro Gly Cys Ala Leu Glu Gln Leu Val Leu Tyr Asp Thr
                420                 425                 430

TAC TGG ACG GAG GAG GTG GAG GAC CGC CTG CAG GCC CTG GAG GGG AGC   1344
Tyr Trp Thr Glu Glu Val Glu Asp Arg Leu Gln Ala Leu Glu Gly Ser
            435                 440                 445

AAG CCC GGC CTG AGG GTC ATC TCC TGA                               1371
Lys Pro Gly Leu Arg Val Ile Ser
450                 455
```

(2) INFORMATION FOR SEQ ID NO:2:

(i) SEQUENCE CHARACTERISTICS:
        (A) LENGTH: 456 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Leu Asp Ile His Cys Glu Gln Leu Ser Asp Ala Arg Trp Thr
1               5                   10                  15

Glu Leu Leu Pro Leu Leu Gln Gln Tyr Glu Val Val Arg Leu Asp Asp
            20                  25                  30

Cys Gly Leu Thr Glu Glu His Cys Lys Asp Ile Gly Ser Ala Leu Arg
        35                  40                  45
```

```
Ala Asn Pro Ser Leu Thr Glu Leu Cys Leu Arg Thr Asn Glu Leu Gly
    50                  55                  60

Asp Ala Gly Val His Leu Val Leu Gln Gly Leu Gln Ser Pro Thr Cys
65                  70                  75                  80

Lys Ile Gln Lys Leu Ser Leu Gln Asn Cys Ser Leu Thr Glu Ala Gly
                85                  90                  95

Cys Gly Val Leu Pro Ser Thr Leu Arg Ser Leu Pro Thr Leu Arg Glu
            100                 105                 110

Leu His Leu Ser Asp Asn Pro Leu Gly Asp Ala Gly Leu Arg Leu Leu
        115                 120                 125

Cys Glu Gly Leu Leu Asp Pro Gln Cys His Leu Glu Lys Leu Gln Leu
    130                 135                 140

Glu Tyr Cys Arg Leu Thr Ala Ala Ser Cys Glu Pro Leu Ala Ser Val
145                 150                 155                 160

Leu Arg Ala Thr Arg Ala Leu Lys Glu Leu Thr Val Ser Asn Asn Asp
                165                 170                 175

Ile Gly Glu Ala Gly Ala Arg Val Leu Gly Gln Gly Leu Ala Asp Ser
            180                 185                 190

Ala Cys Gln Leu Glu Thr Leu Arg Leu Glu Asn Cys Gly Leu Thr Pro
        195                 200                 205

Ala Asn Cys Lys Asp Leu Cys Gly Ile Val Ala Ser Gln Ala Ser Leu
    210                 215                 220

Arg Glu Leu Asp Leu Gly Ser Asn Gly Leu Gly Asp Ala Gly Ile Ala
225                 230                 235                 240

Glu Leu Cys Pro Gly Leu Leu Ser Pro Ala Ser Arg Leu Lys Thr Leu
                245                 250                 255

Trp Leu Trp Glu Cys Asp Ile Thr Ala Ser Gly Cys Arg Asp Leu Cys
            260                 265                 270

Arg Val Leu Gln Ala Lys Glu Thr Leu Lys Glu Leu Ser Leu Ala Gly
        275                 280                 285

Asn Lys Leu Gly Asp Glu Gly Ala Arg Leu Leu Cys Glu Ser Leu Leu
    290                 295                 300

Gln Pro Gly Cys Gln Leu Glu Ser Leu Trp Val Lys Ser Cys Ser Leu
305                 310                 315                 320

Thr Ala Ala Cys Cys Gln His Val Ser Leu Met Leu Thr Gln Asn Lys
                325                 330                 335

His Leu Leu Glu Leu Gln Leu Ser Ser Asn Lys Leu Gly Asp Ser Gly
            340                 345                 350

Ile Gln Glu Leu Cys Gln Ala Leu Ser Gln Pro Gly Thr Thr Leu Arg
        355                 360                 365

Val Leu Cys Leu Gly Asp Cys Glu Val Thr Asn Ser Gly Cys Ser Ser
    370                 375                 380

Leu Ala Ser Leu Leu Ala Asn Arg Ser Leu Arg Glu Leu Asp Leu
385                 390                 395                 400

Ser Asn Asn Cys Val Gly Asp Pro Gly Val Leu Gln Leu Leu Gly Ser
                405                 410                 415

Leu Glu Gln Pro Gly Cys Ala Leu Glu Gln Leu Val Leu Tyr Asp Thr
            420                 425                 430

Tyr Trp Thr Glu Glu Val Glu Asp Arg Leu Gln Ala Leu Glu Gly Ser
        435                 440                 445

Lys Pro Gly Leu Arg Val Ile Ser
    450                 455
```

(2) INFORMATION FOR SEQ ID NO:3:

(i) SEQUENCE CHARACTERISTICS:
        (A) LENGTH: 1374 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..1368

(xi) SEQUENCE DESCRIPTION: SEQ ID NO:3:

```
ATG AGT CTT GAC ATC CAG TGT GAG CAG CTG AGT GAT GCC CGG TGG ACA        48
Met Ser Leu Asp Ile Gln Cys Glu Gln Leu Ser Asp Ala Arg Trp Thr
1               5                  10                  15

GAG CTC CTT CCC CTG ATC CAA CAA TAC CAA GTG GTC AGG CTG GAT GAC        96
Glu Leu Leu Pro Leu Ile Gln Gln Tyr Gln Val Val Arg Leu Asp Asp
                20                  25                  30

TGT GGC CTC ACT GAA GTG CGG TGC AAA GAC ATC AGG TCA GCG ATC CAG       144
Cys Gly Leu Thr Glu Val Arg Cys Lys Asp Ile Arg Ser Ala Ile Gln
        35                  40                  45

GCC AAC CCT GCC CTG ACA GAG CTC AGC CTA CGC ACC AAT GAA CTG GGT       192
Ala Asn Pro Ala Leu Thr Glu Leu Ser Leu Arg Thr Asn Glu Leu Gly
    50                  55                  60

GAT GCT GGT GTG GGT CTG GTG CTC CAG GGC CTG CAG AAT CCC ACT TGT       240
Asp Ala Gly Val Gly Leu Val Leu Gln Gly Leu Gln Asn Pro Thr Cys
65                  70                  75                  80

AAG ATC CAG AAG CTG AGC CTT CAG AAC TGC AGC TTG ACG GAA GCT GGC       288
Lys Ile Gln Lys Leu Ser Leu Gln Asn Cys Ser Leu Thr Glu Ala Gly
                85                  90                  95

TGT GGG GTC CTG CCT GAT GTG CTG CGC TCT TTG TCT ACC CTG CGT GAA       336
Cys Gly Val Leu Pro Asp Val Leu Arg Ser Leu Ser Thr Leu Arg Glu
                100                 105                 110

CTA CAT CTC AAT GAC AAC CCT CTG GGG GAT GAA GGC CTG AAG CTG CTC       384
Leu His Leu Asn Asp Asn Pro Leu Gly Asp Glu Gly Leu Lys Leu Leu
        115                 120                 125

TGT GAA GGA CTC CGG GAC CCC CAG TGC CGT CTT GAG AAG CTT CAG TTG       432
Cys Glu Gly Leu Arg Asp Pro Gln Cys Arg Leu Glu Lys Leu Gln Leu
    130                 135                 140

GAA TAC TGT AAC CTC ACA GCT ACC AGC TGC GAG CCC CTG GCC TCA GTG       480
Glu Tyr Cys Asn Leu Thr Ala Thr Ser Cys Glu Pro Leu Ala Ser Val
145                 150                 155                 160

CTC AGG GTG AAA CCT GAC TTT AAA GAG CTA GTA TTG AGC AAC AAT GAC       528
Leu Arg Val Lys Pro Asp Phe Lys Glu Leu Val Leu Ser Asn Asn Asp
                165                 170                 175

TTC CAT GAG GCT GGT ATC CAC ACT CTG TGC CAG GGC CTG AAG GAT TCT       576
Phe His Glu Ala Gly Ile His Thr Leu Cys Gln Gly Leu Lys Asp Ser
                180                 185                 190

GCC TGT CAA CTG GAG TCA CTC AAA CTG GAG AAC TGT GGT ATC ACA TCA       624
Ala Cys Gln Leu Glu Ser Leu Lys Leu Glu Asn Cys Gly Ile Thr Ser
        195                 200                 205

GCC AAC TGC AAG GAT CTG TGT GAT GTT GTG GCC TCC AAA GCC TCA CTG       672
Ala Asn Cys Lys Asp Leu Cys Asp Val Val Ala Ser Lys Ala Ser Leu
    210                 215                 220

CAA GAA CTG GAC TTG GGC AGC AAC AAG CTG GGC AAC ACA GGC ATT GCA       720
Gln Glu Leu Asp Leu Gly Ser Asn Lys Leu Gly Asn Thr Gly Ile Ala
225                 230                 235                 240

GCA CTG TGC TCA GGA CTG CTG CTT CCC AGC TGC AGG CTG AGG ACT CTG       768
Ala Leu Cys Ser Gly Leu Leu Leu Pro Ser Cys Arg Leu Arg Thr Leu
                245                 250                 255
```

```
TGG CTC TGG GAC TGT GAT GTC ACT GCA GAA GGC TGC AAG GAC CTG TGC      816
Trp Leu Trp Asp Cys Asp Val Thr Ala Glu Gly Cys Lys Asp Leu Cys
        260                 265                 270

CGT GTC CTC AGA GCC AAG CAG AGC CTG AAG GAA CTC AGC CTA GCT GGC      864
Arg Val Leu Arg Ala Lys Gln Ser Leu Lys Glu Leu Ser Leu Ala Gly
        275                 280                 285

AAT GAG CTG AAG GAT GAG GGT GCC CAA CTG CTG TGT GAG AGC CTG TTA      912
Asn Glu Leu Lys Asp Glu Gly Ala Gln Leu Leu Cys Glu Ser Leu Leu
        290                 295                 300

GAG CCT GGC TGT CAG CTG GAG TCA CTG TGG GTA AAG ACC TGT AGC CTC      960
Glu Pro Gly Cys Gln Leu Glu Ser Leu Trp Val Lys Thr Cys Ser Leu
305                 310                 315                 320

ACA GCT GCC TCT TGT CCC CAC TTC TGC TCG GTG TTG ACC AAA AAC AGT     1008
Thr Ala Ala Ser Cys Pro His Phe Cys Ser Val Leu Thr Lys Asn Ser
                325                 330                 335

TCT CTG TTT GAG TTG CAA ATG AGC AGC AAC CCG CTG GGA GAC TCG GGA     1056
Ser Leu Phe Glu Leu Gln Met Ser Ser Asn Pro Leu Gly Asp Ser Gly
        340                 345                 350

GTC GTG GAG CTT TGC AAG GCC CTG GGC TAT CCG GAC ACA GTG CTG CGT     1104
Val Val Glu Leu Cys Lys Ala Leu Gly Tyr Pro Asp Thr Val Leu Arg
        355                 360                 365

GTG CTT TGG CTG GGA GAC TGT GAT GTG ACA GAC AGT GGC TGC AGC AGC     1152
Val Leu Trp Leu Gly Asp Cys Asp Val Thr Asp Ser Gly Cys Ser Ser
        370                 375                 380

CTT GCC ACT GTC CTG CTG GCC AAC CGC AGC TTG AGG GAA CTG GAC CTC     1200
Leu Ala Thr Val Leu Leu Ala Asn Arg Ser Leu Arg Glu Leu Asp Leu
385                 390                 395                 400

AGT AAC AAC TGC ATG GGG GAC AAC GGT GTC CTA CAA CTG CTG GAG AGC     1248
Ser Asn Asn Cys Met Gly Asp Asn Gly Val Leu Gln Leu Leu Glu Ser
                405                 410                 415

CTC AAA CAG CCC AGC TGC ATC CTT CAG CAG CTT GTC CTG TAT GAC ATT     1296
Leu Lys Gln Pro Ser Cys Ile Leu Gln Gln Leu Val Leu Tyr Asp Ile
        420                 425                 430

TAC TGG ACG GAT GAG GTG GAA GAC CAG CTT CGG GCC CTG GAG GAG GAA     1344
Tyr Trp Thr Asp Glu Val Glu Asp Gln Leu Arg Ala Leu Glu Glu Glu
        435                 440                 445

AGG CCA TCC CTG AGG ATC ATT TCC TGATAA                              1374
Arg Pro Ser Leu Arg Ile Ile Ser
450                 455
```

(2) INFORMATION FOR SEQ ID NO:4:

(i) SEQUENCE CHARACTERISTICS:
        (A) LENGTH: 456 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Leu Asp Ile Gln Cys Glu Gln Leu Ser Asp Ala Arg Trp Thr
1               5                   10                  15

Glu Leu Leu Pro Leu Ile Gln Gln Tyr Gln Val Val Arg Leu Asp Asp
            20                  25                  30

Cys Gly Leu Thr Glu Val Arg Cys Lys Asp Ile Arg Ser Ala Ile Gln
        35                  40                  45

Ala Asn Pro Ala Leu Thr Glu Leu Ser Leu Arg Thr Asn Glu Leu Gly
    50                  55                  60

Asp Ala Gly Val Gly Leu Val Leu Gln Gly Leu Gln Asn Pro Thr Cys
65                  70                  75                  80

Lys Ile Gln Lys Leu Ser Leu Gln Asn Cys Ser Leu Thr Glu Ala Gly
```

```
                  85                  90                  95
Cys Gly Val Leu Pro Asp Val Leu Arg Ser Leu Ser Thr Leu Arg Glu
            100                 105                 110

Leu His Leu Asn Asp Asn Pro Leu Gly Asp Glu Gly Leu Lys Leu Leu
            115                 120                 125

Cys Glu Gly Leu Arg Asp Pro Gln Cys Arg Leu Glu Lys Leu Gln Leu
            130                 135                 140

Glu Tyr Cys Asn Leu Thr Ala Thr Ser Cys Glu Pro Leu Ala Ser Val
145                 150                 155                 160

Leu Arg Val Lys Pro Asp Phe Lys Glu Leu Val Leu Ser Asn Asn Asp
                165                 170                 175

Phe His Glu Ala Gly Ile His Thr Leu Cys Gln Gly Leu Lys Asp Ser
            180                 185                 190

Ala Cys Gln Leu Glu Ser Leu Lys Leu Glu Asn Cys Gly Ile Thr Ser
            195                 200                 205

Ala Asn Cys Lys Asp Leu Cys Asp Val Val Ala Ser Lys Ala Ser Leu
            210                 215                 220

Gln Glu Leu Asp Leu Gly Ser Asn Lys Leu Gly Asn Thr Gly Ile Ala
225                 230                 235                 240

Ala Leu Cys Ser Gly Leu Leu Leu Pro Ser Cys Arg Leu Arg Thr Leu
                245                 250                 255

Trp Leu Trp Asp Cys Asp Val Thr Ala Glu Gly Cys Lys Asp Leu Cys
            260                 265                 270

Arg Val Leu Arg Ala Lys Gln Ser Leu Lys Glu Leu Ser Leu Ala Gly
            275                 280                 285

Asn Glu Leu Lys Asp Glu Gly Ala Gln Leu Leu Cys Glu Ser Leu Leu
            290                 295                 300

Glu Pro Gly Cys Gln Leu Glu Ser Leu Trp Val Lys Thr Cys Ser Leu
305                 310                 315                 320

Thr Ala Ala Ser Cys Pro His Phe Cys Ser Val Leu Thr Lys Asn Ser
                325                 330                 335

Ser Leu Phe Glu Leu Gln Met Ser Ser Asn Pro Leu Gly Asp Ser Gly
            340                 345                 350

Val Val Glu Leu Cys Lys Ala Leu Gly Tyr Pro Asp Thr Val Leu Arg
            355                 360                 365

Val Leu Trp Leu Gly Asp Cys Asp Val Thr Asp Ser Gly Cys Ser Ser
370                 375                 380

Leu Ala Thr Val Leu Leu Ala Asn Arg Ser Leu Arg Glu Leu Asp Leu
385                 390                 395                 400

Ser Asn Asn Cys Met Gly Asp Asn Gly Val Leu Gln Leu Leu Glu Ser
            405                 410                 415

Leu Lys Gln Pro Ser Cys Ile Leu Gln Gln Leu Val Leu Tyr Asp Ile
            420                 425                 430

Tyr Trp Thr Asp Glu Val Glu Asp Gln Leu Arg Ala Leu Glu Glu Glu
            435                 440                 445

Arg Pro Ser Leu Arg Ile Ile Ser
450                 455

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear
```

-continued (ii) MOLECULE TYPE: cDNA (xi) SEQUENCE DESCRIPTION: SEQ ID NO:5:

TAATAGCATA TGAGTCTTGA CATCCAGTGT GAG    33

(2) INFORMATION FOR SEQ ID NO:6:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TTATTAGGAT CCTTATCAGG AAATGATCCT CAGGGATGGC C    41

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

TATTATCATA TGAACCTSGA YATYCAYTGY GA    32

(2) INFORMATION FOR SEQ ID NO:8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

TATTATAAGC TTGCCCAAAA GGTGTTTTAC TAAGTAG    37